(12) United States Patent
Kale et al.

(10) Patent No.: US 10,362,997 B2
(45) Date of Patent: Jul. 30, 2019

(54) SYSTEM AND METHOD OF EXTRACTION, IDENTIFICATION, MARKING AND DISPLAY OF HEART VALVE SIGNALS

(71) Applicant: AventuSoft, LLC, Boca Raton, FL (US)

(72) Inventors: Kaustubh Kale, Royal Palm Beach, FL (US); Luis Gonzalo Sanchez Giraldo, Miami, FL (US)

(73) Assignee: Aventusoft, LLC, Boca Raton, FL (US)

( * ) Notice: Subject to any disclaimer, the term of this patent is extended or adjusted under 35 U.S.C. 154(b) by 49 days.

(21) Appl. No.: 15/397,005

(22) Filed: Jan. 3, 2017

(65) Prior Publication Data

US 2017/0188862 A1    Jul. 6, 2017

Related U.S. Application Data

(60) Provisional application No. 62/274,761, filed on Jan. 4, 2016, provisional application No. 62/274,763, filed
(Continued)

(51) Int. Cl.
*A61B 5/00* (2006.01)
*A61B 5/0404* (2006.01)
(Continued)

(52) U.S. Cl.
CPC .......... *A61B 5/7282* (2013.01); *A61B 5/0006* (2013.01); *A61B 5/0008* (2013.01);
(Continued)

(58) Field of Classification Search
None
See application file for complete search history.

(56) References Cited

U.S. PATENT DOCUMENTS

| 7,096,061 B2 | 8/2006 | Arad |
| 7,174,203 B2 | 2/2007 | Arand et al. |

(Continued)

OTHER PUBLICATIONS

Aharon et al., "K-SVD: An Algorithm for Designing Overcomplete Dictionaries for Sparse Representation," IEEE Transactions on Signal Processing, vol. 54, No. 11, pp. 4311-4322 (Nov. 2006).*
(Continued)

*Primary Examiner* — Christopher Koharski
*Assistant Examiner* — Elizabeth K So
(74) *Attorney, Agent, or Firm* — Pablo Meles

(57) ABSTRACT

A system (100) for monitoring and diagnosing heart conditions includes a sensor array (102) with accelerometers, an electrocardiogram sensor, and a system to synchronously capture and process (103, 105, or 106) composite heart signals. The system performs separation, identification and marking (201-205 or 501-509) of the signals, to extract information in cardiac vibrations. Machine learning, auditory scene analysis, or spare coding approaches can be used to resolve source separation problems. Analysis of the composite signals separates different vibration signals (302, 303, 304, 305), identifies streams for particular valve signal, and marks them with event time information with respect to a synchronous electrocardiogram signal (306). The psychoacoustic analysis mimics human auditory processing to enhance hearing of heart valve sounds by separating valve vibrations from the composite signal, and providing extraction, identification, marking and display of individual valve signals.

13 Claims, 6 Drawing Sheets

Related U.S. Application Data on Jan. 4, 2016, provisional application No. 62/274,765, filed on Jan. 4, 2016, provisional application No. 62/274,766, filed on Jan. 4, 2016, provisional application No. 62/274,770, filed on Jan. 4, 2016.

(51) Int. Cl.

| | | |
|---|---|---|
| *A61B 5/0456* | (2006.01) | |
| *A61B 5/0205* | (2006.01) | |
| *A61B 5/0468* | (2006.01) | |
| *A61B 5/024* | (2006.01) | |
| *A61B 5/04* | (2006.01) | |
| *A61B 5/0432* | (2006.01) | |
| *A61B 5/11* | (2006.01) | |
| *A61B 5/02* | (2006.01) | |
| *G06F 19/00* | (2018.01) | |
| *G16H 40/67* | (2018.01) | |
| *A61B 7/04* | (2006.01) | |
| *A61B 5/08* | (2006.01) | |

(52) U.S. Cl.
CPC .......... *A61B 5/0022* (2013.01); *A61B 5/0205* (2013.01); *A61B 5/02028* (2013.01); *A61B 5/02444* (2013.01); *A61B 5/0404* (2013.01); *A61B 5/04014* (2013.01); *A61B 5/04017* (2013.01); *A61B 5/0456* (2013.01); *A61B 5/0468* (2013.01); *A61B 5/04325* (2013.01); *A61B 5/1102* (2013.01); *A61B 5/6801* (2013.01); *A61B 5/6802* (2013.01); *A61B 5/6831* (2013.01); *A61B 5/6833* (2013.01); *A61B 5/7214* (2013.01); *A61B 5/7225* (2013.01); *A61B 7/04* (2013.01); *G06F 19/00* (2013.01); *G16H 40/67* (2018.01); *A61B 5/024* (2013.01); *A61B 5/02055* (2013.01); *A61B 5/0816* (2013.01); *A61B 2562/0204* (2013.01); *A61B 2562/0219* (2013.01); *A61B 2562/06* (2013.01)

(56) References Cited

U.S. PATENT DOCUMENTS

| | | |
|---|---|---|
| 7,351,207 B2 | 4/2008 | Priemer |
| 8,105,241 B2 | 1/2012 | Nelson et al. |
| 8,131,354 B2 | 3/2012 | Arad |
| 8,251,911 B2 | 4/2012 | MacQuarrie et al. |
| 8,255,042 B2 | 8/2012 | MacQuarrie et al. |
| 8,290,577 B2 | 10/2012 | Brooks et al. |
| 8,475,396 B2 * | 7/2013 | Jones ............ A61B 7/026 600/586 |
| 8,614,630 B2 | 12/2013 | Narasimhan et al. |
| 8,688,202 B2 | 4/2014 | Brockway et al. |
| 8,694,089 B2 | 5/2014 | Arad |
| 8,715,206 B2 | 5/2014 | Telfort et al. |
| 8,764,653 B2 | 7/2014 | Kaminska et al. |
| 8,790,259 B2 | 7/2014 | Katra et al. |
| 8,823,490 B2 | 9/2014 | Libbus et al. |
| 8,868,175 B2 | 10/2014 | Arad |
| 8,898,369 B1 | 11/2014 | Yang |
| 9,035,794 B2 | 5/2015 | Narasimhan et al. |
| 9,247,004 B2 | 1/2016 | Azimi et al. |
| 9,307,908 B2 | 4/2016 | Chan et al. |
| 9,370,335 B2 | 6/2016 | Al-Ali et al. |
| 9,445,719 B2 | 9/2016 | Libbus et al. |
| 9,462,994 B2 | 10/2016 | Rogers et al. |
| 2004/0006279 A1 | 1/2004 | Arad |
| 2006/0095085 A1 | 5/2006 | Marcus et al. |
| 2007/0219059 A1 | 9/2007 | Schwartz et al. |
| 2007/0273504 A1* | 11/2007 | Tran ............ A61B 5/0022 340/539.12 |
| 2011/0263994 A1 | 10/2011 | Burns et al. |
| 2012/0209131 A1 | 8/2012 | Jones et al. |
| 2013/0109989 A1 | 5/2013 | Busse et al. |
| 2013/0245487 A1 | 9/2013 | Aga |
| 2013/0281875 A1 | 10/2013 | Narasimhan et al. |
| 2014/0019080 A1 | 1/2014 | Chan et al. |
| 2014/0066795 A1 | 3/2014 | Ferdosi et al. |
| 2014/0073982 A1 | 3/2014 | Yang et al. |
| 2014/0200474 A1 | 7/2014 | Selvaraj et al. |
| 2014/0275932 A1 | 9/2014 | Zadig |
| 2014/0276127 A1 | 9/2014 | Ferdosi et al. |
| 2015/0020571 A1 | 1/2015 | Chan et al. |
| 2015/0038856 A1 | 2/2015 | Houlton et al. |
| 2015/0045628 A1 | 2/2015 | Moghadam et al. |
| 2015/0065894 A1 | 3/2015 | Yiopisto |
| 2015/0164410 A1 | 6/2015 | Selvaraj et al. |
| 2015/0164411 A1 | 6/2015 | Selvaraj et al. |

OTHER PUBLICATIONS

Capan; Bernstein, et al.; Measurement of Ejection Fraction by Bioimpedeance . . . , Critical Care Med.; Apr. 1987, vol. 15, Issue 4, p. 402.

W. Chan M. Woldeyohannes et al.; Haemobdynamic and structural correlates . . . ; BMJ Open 2013;3:e002660.

C.L. Garrard, Jr et al.; The Relationship of Alterations in Systolic . . . : Circulation. 1970; vol. 42; pp. 455-462; Amer. Heart Ass.

S. Toggweiler et al: Monitoring anthracycline chemotherapy patients; 2013; Clin. Cariol.; vol. 36, Issue 4, pp. 201-206.

S. Wang et al: Rapid Bedside Identification of high risk population; International J. of Cardiology; Jan. 24, 2013; vol. 168, pp. 1881-1886.

* cited by examiner

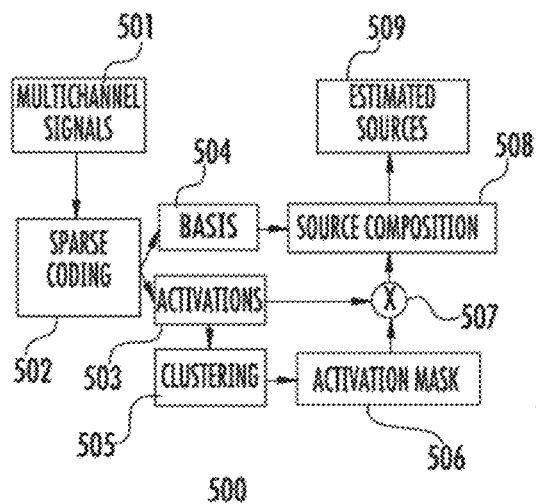
FIG. 5A
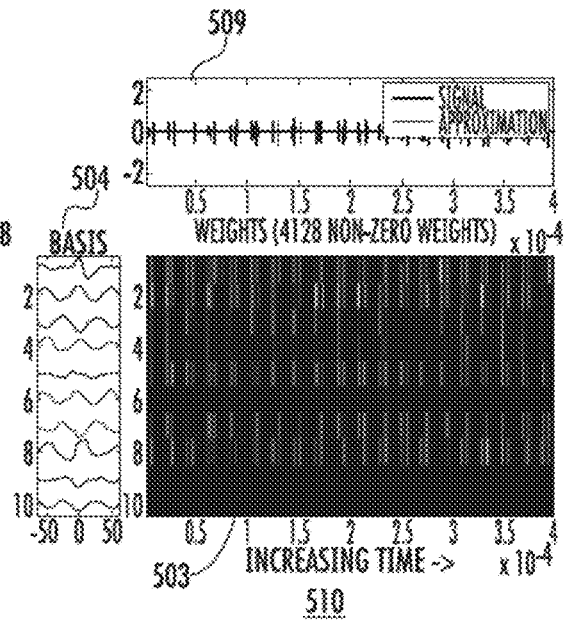
FIG. 5B
FIG. 5C
FIG. 5D

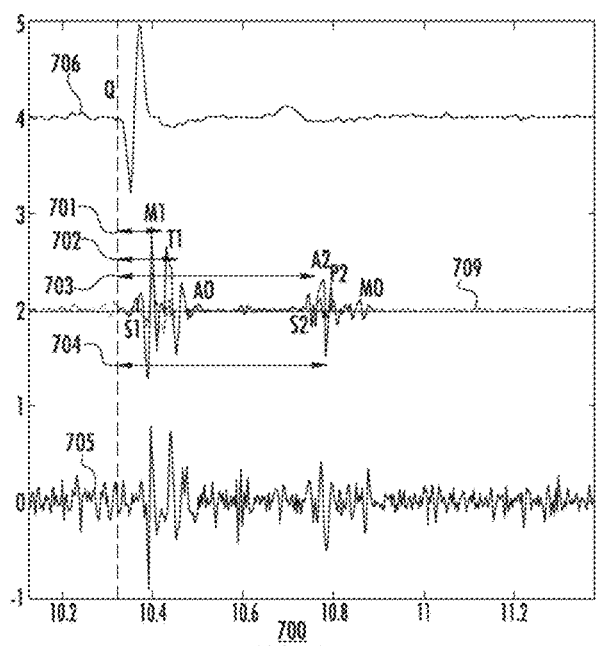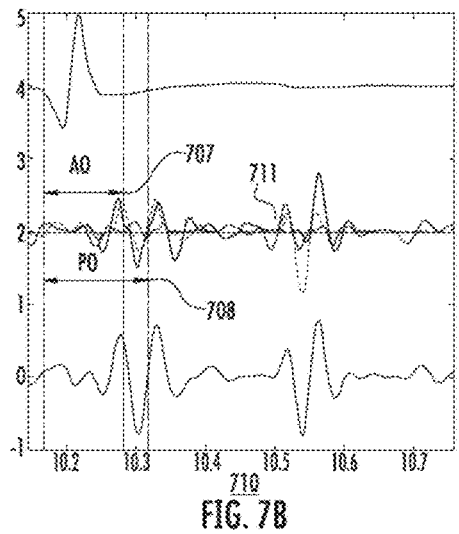
FIG. 7A
FIG. 7B

SYSTEM AND METHOD OF EXTRACTION, IDENTIFICATION, MARKING AND DISPLAY OF HEART VALVE SIGNALS

CROSS REFERENCE TO RELATED APPLICATIONS

This Application claims the priority benefit of Provisional Application Nos. 62/274,761, 62/274,763, 62/274,765, 62/274,766, and 62/274,770, each of which were filed on Jan. 4, 2016, the entire disclosure of each are incorporated herein by reference.

FIELD

The embodiments herein relate generally to cardiac health monitoring and more particularly to analysis software combined with transducers to capture multi-channel vibration signals along with an electrocardiogram signal for the measurement of heart functions.

BACKGROUND

Heart disease is the leading cause of death accounting for more than one-third (33.6%) of all U.S. deaths. Overall cardiac health can be significantly improved by proper triage. Low invasive and non-invasive ultrasound techniques (e.g., echocardiogram) are standard procedures, but the requirement of expensive devices and skilled operators limit their applicability. The following are the various types of heart disease that can be diagnosed and treated using the separated signal, namely, Coronary artery disease, Heart murmurs and valve abnormalities, Heart failure, Heart rhythm abnormalities (arrhythmias), Vascular disease, congenital heart disease, Cardiac resynchronization and Risk factor modification. A physician can work with patients to perform a comprehensive evaluation and design a personalized plan of care aimed at keeping them healthy.

The cardiohemic system which consists of the heart walls, valves and blood, creates vibrations during each cardiac cycle. The vibrations are the result of the acceleration and deceleration of blood due to abrupt mechanical opening and closing of the valves during the cardiac cycle.

SUMMARY

The exemplary embodiments herein provide a method and system based on a technique of separating, identifying and marking the heart signals, to extract information contained in cardiac vibration objects. Machine learning, auditory scene analysis, or spare coding are approaches to the source separation problem. Further note that the techniques and methods herein are not limited to acoustic, electrical or vibrational data as might be used in some stethoscopes, but can also be applied to other forms of monitoring such as echo imaging or sonograms, magnetic resonance imaging (MRI), computed tomography (CT) scanning, positron emission tomography (PET) scanning, and monitoring using various forms of catheterization. The techniques and methods herein are primarily applicable to monitoring of heart valve events, but can be alternatively applied to other types of involuntary biological signaling emanating from the brain, intrauterine, pre-natal contractions, or elsewhere within both humans and other species.

Examples of vibration objects are Mitral valve opening and closing, Aortic valve opening and closing, Pulmonary valve opening and closing, Tricuspid valve opening and closing, and heart wall motions. A portion of the energy produced by these vibrations lies in the infra-sound range, which falls in the inaudible and low sensitivity human hearing range. A portion of the energy produced by these vibrations falls in the audible hearing range. For example, the vibration objects from the Mitral, Tricuspid, Aortic, and Pulmonary valve openings fall in a lower range of vibrations such as 0 to 60 Hertz, whereas vibration objects from the Mitral, Tricuspid, Aortic, and Pulmonary valve closings fall in a higher range of vibrations such as 50 to 150 Hertz. Accelerometer transducers placed on the chest capture these vibrations from both these ranges. Data is obtained using a tri-axial accelerometer or multiple tri-axial accelerometers placed on different points of a torso of a subject.

Source separation analysis in accordance with the methods described herein extract individual vibration objects from the composite vibration signal captured on the surface. The individual vibration signals are identified to be from the mitral valve, aortic valve, tricuspid valve, and the pulmonary valve during individual heart beats. Along with separating breathing sounds, and heart wall motion. The identified valve signals are marked to indicate their start and end of the event with respect to the start of the electrocardiogram (EKG). This event corresponds to the opening and closing of each valve. The individual vibration signals are identified to be from the mitral valve, aortic valve, tricuspid valve, the pulmonary valve, coronary artery, murmurs, third sound, fourth sound, respiratory sound, breathing, and snoring during individual heart beats.

DESCRIPTION OF THE DRAWINGS

FIG. 5A illustrates the schematic of the source separation approach of extracting individual vibration objects or each valve into individual streams in accordance with one embodiment;

FIG. 5B illustrates graphic representations of the basis and activations used for the source separation approach of FIG. 5A in accordance with one embodiment;

FIG. 5C shows a convolutional version of a matching pursuit algorithm to infer the activation of a given set of basis functions for use in the source separation approach of FIG. 5A in accordance with one embodiment;

FIG. 5D shows a K-SVD algorithm to refine a set of basis elements given the desired signal and a set of activations for use in the source separation approach of FIG. 5A in accordance with one embodiment;

FIGS. 7A and 7B illustrate the marking of vibration objects or each valve into individual streams in accordance with one embodiment.

DETAILED DESCRIPTION

Figure 1A:
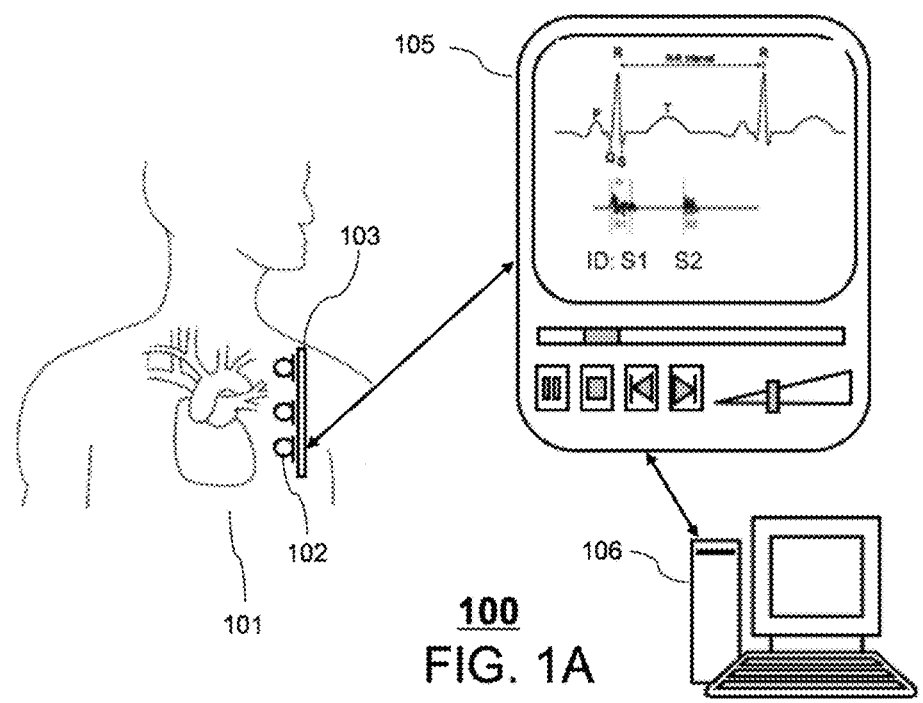
FIG. 1A illustrates a system for the extraction, identification, marking and display of the heart valve signals in accordance with one embodiment.

The exemplary embodiments may be further understood with reference to the following description and the appended drawings, wherein like elements are referred to with the same reference numerals. The exemplary embodiments describe a system and method of extraction, identification, marking and display of the heart valve signals. Specifically, psychoacoustics are considered in separating cardiac vibration signals captured through the transducers. The system, the psychoacoustics, and a related method will be discussed in further detail below.

The exemplary embodiments provide a novel approach for small, portable, robust, fast and configurable source separation based software with transducer hardware. The use of the vibration signal pattern and novel psychoacoustics help bypass conventional issues faced by linear time invariant systems.

The signals of the biomechanical system show a high clinical relevance when auscultated on the chest. The heart and lung sounds are applied to the diagnosis of cardiac and respiratory disturbances, whereas the snoring sounds have been acknowledged as important symptoms of the airway obstruction. The innovation here provides extraction of all three types of body sounds from the composite vibration captured at the skin. The exemplary embodiments of the system and method proposed here for source separation can use the composite signal capture via different transducers not limited to accelerometer, acoustic, or piezoelectric 102. Any of these act as an electro-acoustic converter to establish a body sound for processing. The source separation provides the capability to extract signals while operating in a medium that is non-linear and time variant.

Figure 1B:
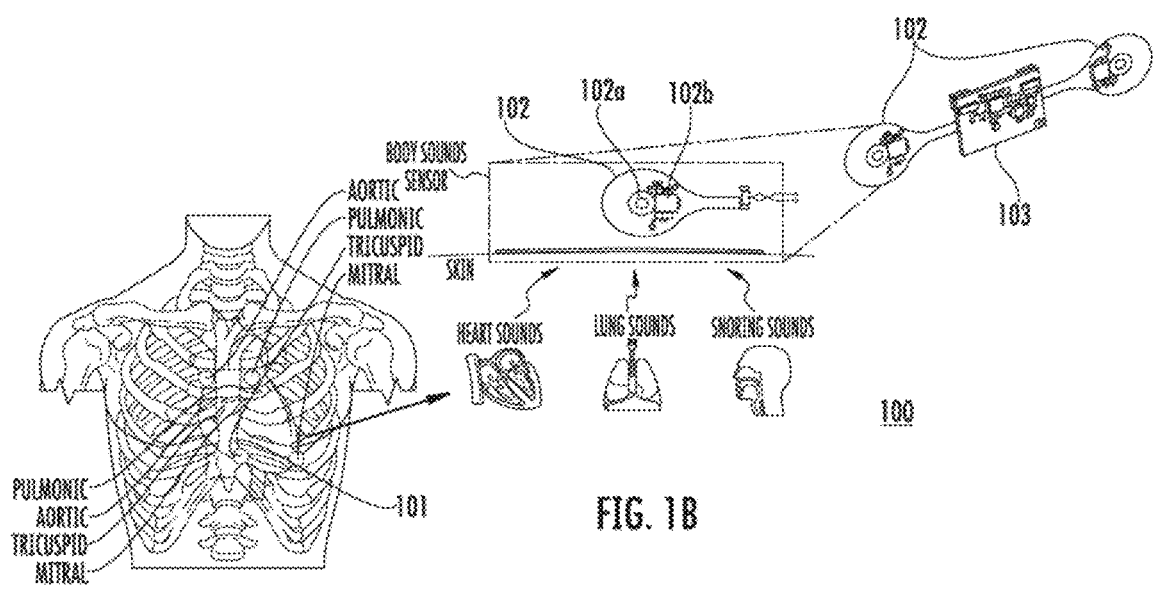
FIGS. 1B and 1C illustrate a more detailed view of the system for extraction, identification, marking and display of heart valve signals in accordance with one embodiment.
Figure 1C:
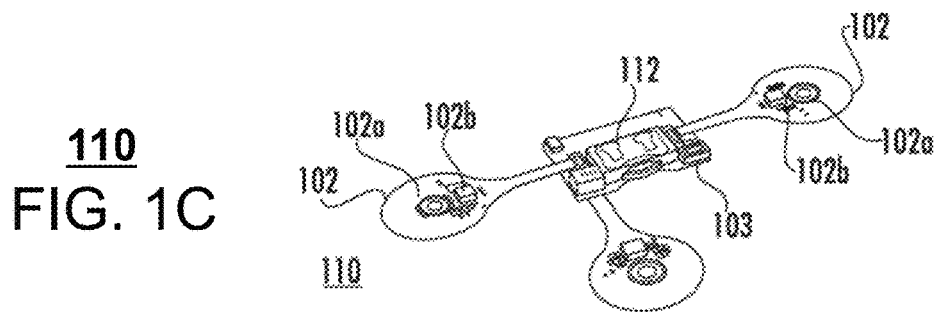

The exemplary embodiments of the system and method proposed here are shown in FIGS. 1A, 1B and 1C. A system 100 is an embedded platform which can be any smart processing platform with digital signal processing capabilities, application processor, data storage, display, input modality like touch-screen or keypad, microphones, speaker, Bluetooth, and connection to the internet via WAN, Wi-Fi, Ethernet or USB or other wireless or wired connection. This embodies custom embedded hardware, smartphone, iPad-like and iPod-like devices. Area 101 in FIGS. 1A and 1B represents the auditory scene at the chest locations. A transducer array 102 captures the heart signal. In some embodiments, the transducer array 102 includes vibration sensors such as accelerometers. In some embodiments, the transducer array includes a pad that includes a vibration sensor such as a vibration sensor 102b and an electrode 102a for an ECG sensor. In some embodiments, the transducer array can include a single pad, two pads as shown in FIG. 1B or more than two pads as shown in FIG. 1C. In the particular embodiment of FIG. 1C, a transducer array 110 includes three pads (102) where each pad includes the vibration sensor 102b and the ECG electronic 102a. Other embodiments can include three or more pads where each pad would have at least a vibration sensor and optionally an electrode for the ECG sensor. A wearable microprocessor hardware module 103 can include digital signal processing capabilities, application processor, Analog to digital frontend, data storage, input modality like buttons, and wired or wireless connection via Bluetooth, Bluetooth low energy, near field communication transceiver, Wi-Fi, Ethernet or USB. The module 103 comprises of the signal processing module 112 on the wearable microprocessor hardware module 103 that captures synchronized sensor data from the transducer array 102. The module saves the captured synchronized sensor data to memory and communicates with the system 100 for data transfer. A module 105 communicatively coupled to the module 103 can calculate vital signs from the input sensor stream coming from the module 103 for the Heart rate, breathing rate, EKG signal, skin temperature, and associated vitals. The module 105 can encrypt the raw sensor data for transmission to a cloud computing module 106. The module 105 also communicates with a dashboard on 106 for data exchange, login, alerts, notifications, display of processed data. Module 106 in FIG. 1 serves as the cloud module that processes the individual streams for eventual source separation, identification and marking of the heart valve signals. In some embodiments, the system 100 i allows a user to visually see the individual streams and information from the heart valves and in some embodiments the system could present streams or information on a connected display or any other modality of display. The transducer array 102 can include multiple sensor transducers that capture the composite signal that includes the electrocardiogram signals, heart sounds, lung sounds and snoring sounds for example. The module 103 can be in the form of wearable hardware that synchronously collects the signals across the transducers and is responsible for the analog to digital conversion, storage and transmission to a portable unit 104. Note that the embodiments herein are not limited to processing the individual streams for source separation, identification and marking of the heart valve signals at the cloud computing module 106 only. Given sufficient processing power, the aforementioned processing can occur at the microprocessor hardware module 103, at the module 105, or at the cloud-computing module 106, or such processing can be distributed among such modules 103, 105, or 106.

Figure 2:
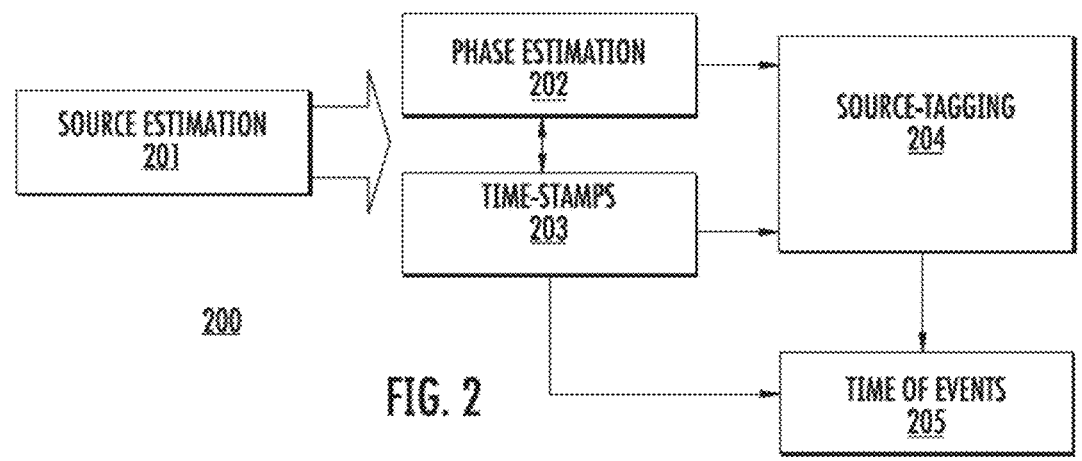
FIG. 2 is a flowchart of a method practiced by the system in accordance with one embodiment.

The exemplary embodiments of the system 200 and method proposed here for the source extraction, identification, and marking of the heart valve signals are shown in FIG. 2. Block 201 indicates the separation of sources from the composite signals which is done by source estimation using, for example, machine learning, auditory scene analysis, or sparse coding. Block 202 represents the phase estimation between the separated sources at each of the sensor positions. Block 203 represents calculating the time stamps of individual sources at each heartbeat with respect to the synchronized EKG signal and the other sensor or sensors. Block 204 represents the source identification module responsible for tagging each of the separated source in individual heart beats to be one of the heart valve event, namely the Mitral valve closing and opening, the Tricuspid valve closing and opening, the Aortic valve opening and closing, and the Pulmonic valve opening and closing. Block 205 represents the time marking module to estimate the time of occurrence of the above-mentioned valve events with respect to the start of the EKG signal.

Figure 3:
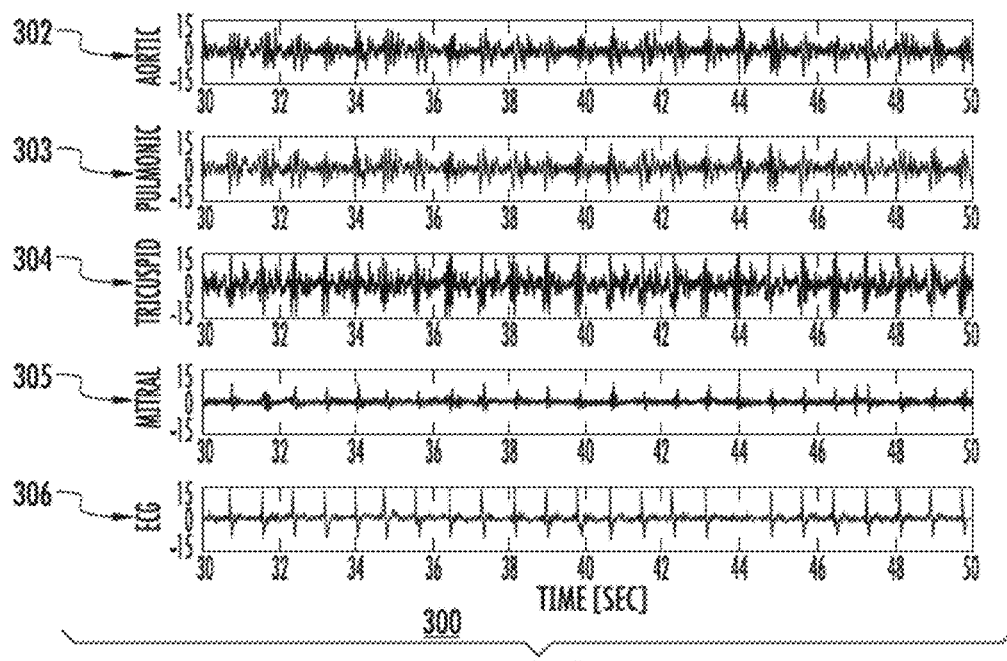
FIG. 3 illustrates multichannel signals captured from the sensor array on the chest shown in accordance with one embodiment.

The exemplary embodiments of the system and method proposed here for the source extraction, identification, and marking of the heart valve signals from a composite signal 300 are shown in FIG. 3. Area(s) 301 illustrated in FIG. 3 indicates the locations at which the composite heart signal can be captured. A vibration signal 302 as charted on the first line of FIG. 3 represents a signal captured at the aortic auscultation location. A vibration signal 303 represents a signal captured at the pulmonic auscultation location. A vibration signal 304 represents a signal captured at the tricuspid auscultation location. A vibration signal 305 represents a signal captured at the mitral auscultation location. The last or bottom line in FIG. 3 represents an electrocardiogram signal 306 captured. In some embodiments, note that the number of sensors used (such as in the sensor array 102 of FIG. 1), are less than the number of vibration sources. For example, 3 sensors can be used to ultimately extract signals for 4 (or more) vibration sources; or 2 sensors can be used to ultimately extract signals for 3 or 4 (or more) vibration sources; or 1 sensor can be used to ultimately extract signals for 2, or 3, or 4 (or more) vibration sources.

Figure 4:
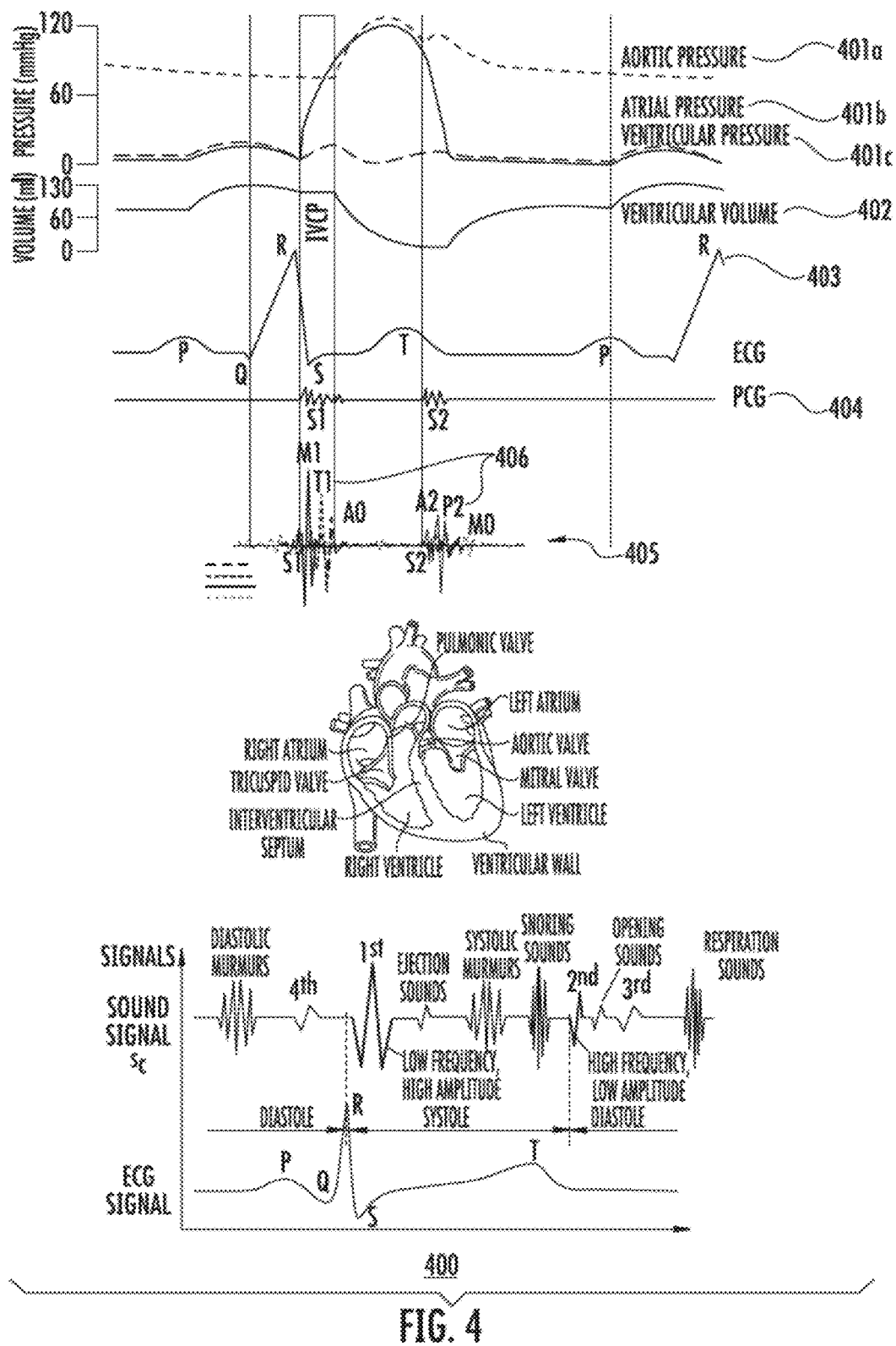
FIG. 4 illustrates a cardiac cycle in relation with Electrocardiogram, acoustic and accelerometer sensors of the system in accordance with one embodiment.

The exemplary embodiments of the system and method proposed here draw inspirations from biology with respect to the cardiac cycle in-relation with electrocardiogram and accelerometer transducer captured cardiac signal. A timeline chart 400 in FIG. 4 shows a cardiac cycle. Lines or signals 401a, 401b, and 401c represent or indicate the pressure changes during a cardiac cycle for aortic pressure (401a), atrial pressure (401b) and ventricular pressure (401c) measured in measured in millimeters of mercury (mmHg). Line or signal 402 represents or indicates the volume changes during a cardiac cycle in milliliters (ml). Line or signal 403 represents or indicates the electrical changes during a cardiac cycle captured by an electrocardiogram. Line or signal 404 represents or indicates the acoustic changes during a cardiac cycle captured by an acoustic sensor such as in a phonocardiogram or PCG. S1 represents the first heart sound or the "lub" sound and the S2 represents the second heart sound or "dub" sound. Line or signal 405 represents or indicates the vibration changes during a cardiac cycle captured by an accelerometer transducer at the location of our device. Pattern 406 indicates the different valve opening and closing seen in line or signal 405 as captured by the accelerometer sensor or sensors. More specifically, a closer inspection of the pattern 406 reveals the closing of the mitral valve (M1) and tricuspid valve (T1) during the S1 or first heart sound and the closing of the aortic valve (A2) and pulmonary valve (P2). The bottom half of FIG. 4, goes on to further show a representation of the anatomy of the human heart relevant for the generation of the sounds and a corresponding graph representing the sounds belonging to coronary artery, murmurs, first sound, second sound, third sound, fourth sound, ejection sounds, opening sounds, respiratory sound, breathing, and snoring during individual heart beats, with respect to the electrocardiogram signal. Briefly, during S1, blood flows in from the pulmonary veins and fills the left atrium and causes the mitral valve to temporarily (open and close) provide access to the left ventricle while almost simultaneously the blood from the superior vena cava fills the right atrium and causes the tricuspid valve to temporarily (open and close) provide access to the right ventricle. The left and right ventricles subsequently fill up with blood and during S2 the aortic valve and pulmonary valves each open and close in quick succession as blood is pumped towards the aorta and pulmonary artery respectively. The first heart sound (S1) when recorded by a high-resolution phonocardiography (PCG) can consist of 5 sequential components that first includes small low frequency vibrations, usually inaudible, that coincide with the beginning of left ventricular contraction, second, includes a large high-frequency vibration, easily audible related to mitral valve closure (M1), third, includes a second high frequency component closely following M1 and related to tricuspid valve closure T1, fourth, S1 includes small frequency vibrations that coincide with the acceleration of blood into the great vessel at the time of aortic valve opening A0, and fifth, S1 includes small frequency vibrations that coincide with the acceleration of blood into the great vessel at the time of pulmonic valve opening P0. The two major audible components are the louder M1 best heard at the apex followed by T1 heard best at the left lower sternal border. They are separated by only 20-30 ms and at the apex are only appreciated as a single sound in the normal subject as the aforementioned "Lub". The second heart sound (S2) have two major components A2 and the P2 are coincident with the incisura of the aorta and pulmonary artery pressure trace, respectively, and terminate the right and left ventricular ejection periods. Right ventricular ejection begins prior to left ventricular ejection, has a longer duration, and terminates after left ventricular ejection, resulting in P2 normally occurring after the A2 as shown in the pattern 406. The first high-frequency component of both A2 and P2 is coincident with the completion of closure of the aortic and pulmonary valve leaflets. As with sounds arising from the AV valves, A2 and P2 are not due to the clapping together of the valve leaflets but are produced by the sudden deceleration of retrograde flow of the blood column in the aorta and pulmonary artery when the elastic limits of the tensed leaflets are met. This abrupt deceleration of flow sets the cardio hemicsystem in vibration. The higher frequency components result in A2 and P2. Followed by the A2 and P2 are the vibrations associated with the valve openings. S2 includes small frequency vibrations that coincide with the acceleration of blood into the left ventrical at the time of mitral valve opening M0, and S2 includes small frequency vibrations that coincide with the acceleration of blood into the right ventrical at the time of tricuspid valve opening T0.

The exemplary embodiments of the system and accompanying method proposed herein provide a source separation analysis algorithm that allows for the separation of the vibrations from the cardiohemic system as illustrated in the system 500 of FIG. 5A and corresponding chart cluster 510 of FIG. 5B. One of the proposed embodiments uses a separation algorithm via a two stage process. First, the signals such as multichannel signals 501 are decomposed using sparse coding 502 into components that appear sparsely across a time chart 503 and further provide sparse activation patterns 504. Then, cluster analysis 505 on the sparse activation patterns 504 is performed. Time locations of activations patterns that are clustered together get assigned to the same source as shown in timeline 509. Finally, activations assigned to the same cluster using an activation mask 506 and multiplier 507 are used along with the basis elements (504) to recompose the sources as the source composition 508. Estimated sources 509 can be determined or extracted from the source composition 508. Method 500 depicts the steps involved in the process. The boxes 502, 505, and 508 are considered computational modules and the boxes 501, 503, 504, 506 and 509 denote data which is either input or output to each module. In one implementation as shown in the algorithm 520 of FIG. 5C, we used a convolutional version of the matching pursuit algorithm to infer the activation of a given set of basis functions, and the K-SVD algorithm 530 of FIG. 5D to refine a set of basis elements given the desired signal and a set of activations. In applied mathematics, K-SVD is a dictionary learning algorithm for creating a dictionary for sparse representations, via a singular value decomposition approach. K-SVD is a generalization of the k-means clustering method, and it works by iteratively alternating between sparse coding the input data based on the current dictionary, and updating the atoms in the dictionary to better fit the data. For clustering, employment of a k-means algorithm on a set of altered activation patterns can be used. The pseudo code for the matching pursuit algorithm is shown in 506 and the pseudo code for the KSVD is shown in 507. The embodiments can include different source separation techniques specifically used for extracting the valve heart signals for application in a non-linear time variant system, where the number of sensors is less than the number of sources, such as, Determined Models, Principal Component Analysis (PCA), Independent Component Analysis ICA, Singular Value Decomposition (SVD), Bin-wise Clustering and Permutation posterior probability Alignment, Undetermined Models, Sparseness condition, Dictionary learning, Convolutive models, and K-SVD Matching Pursuit.

Figures 6A, 6B, 6C:
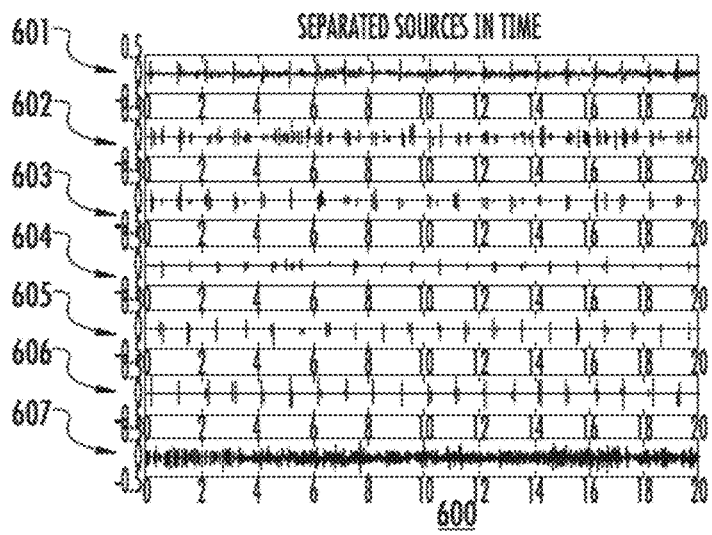
FIGS. 6A, 6B, and 6C illustrate the identification of vibration objects or each valve into individual streams in accordance with one embodiment.

The exemplary embodiments of the system and method proposed here provide a source identification algorithm for the vibrations from the cardiohemic system. Referring to FIG. 6A, in order to find the time stamps for events such as Mitral closing & opening, Tricuspid closing & opening, Aortic opening & closing, Pulmonic opening and closing, we look at all individual source separated (SS) signals 601 to 606 of a composite signal 607 and first try to find the location of max peak in the SS signal for each source and then find delay between two channels. The chart 608 of FIG. 6B shows the frequency spectrum of the corresponding source separated signals. Cross correlated vibrations in aortic and pulmonic channels for each interval for each source are calculated to find a consistent delay between two channels as represented by chart 609 of FIG. 6C. Given the start of a QRS complex (indicative of ventricular depolarization triggered by contraction of the ventricles) and end point of each vibration, the vibration(s) within this interval is cross correlated with all vibrations in each source. This is done for both aortic and pulmonic channels. At the end, Principle Component Analysis (PCA) was applied to find the timing information and delay between two channels. PCA uses SS signal from each source in each channel to find the template which represents a majority of the vibrations within that source. The template is then cross correlated with the whole source and a maximum of PCA signal in each interval is found and compared with the start of QRS. In another implementation, In the second attempt, SS signals from two channels but the same source are fed into PCA to find the template. Then an aortic template is used for both channels' cross correlation to identify the different vibrations into valve events, breathing sounds, and vibrations of the heart walls. To accurately estimate M1, T1, A2, P2, A0, P0 from the frequency signal captured by the digital accelerometer on the wearable microprocessor hardware module, several sub-frequencies are considered. Some are noted here for example: 0-30 Hz, 0-60 Hz, 30-150 hz, 30-250 Hz.

The exemplary embodiments of the system and method proposed here provide a source marking algorithm for the vibrations from the cardiohemic system. Next step is to use PCA to determine which source is associated with which event (Mitral closing & opening, Tricuspid closing & opening, Aortic opening & closing, Pulmonic opening and closing). The following is a description of the architecture for automatic source tagging and timing of valvular events. One way to identify which events are relevant to a source is by manually tagging the sources against the synchronized EKG signal and taking advantage of the timings relative to the QRS wave (identification of the S1 and S2 sounds using the EKG signal as the reference has been widely researched in studies). Another approach is an automatic tagging algorithm. The tagging is composed of a classifier preceded by a feature extraction algorithm. For the timing, we exploit the computations of one of the feature extraction algorithms to obtain an energy contour from which the time location of a given event can be inferred. Because our work builds upon having the ability to capture the signal at different locations simultaneously, we want to exploit the relations among channels to extract additional information about the sources. Likewise some source separation algorithms where channel relations are associated with location, the embodiments herein can leverage on the intrinsic relations among the channels to extract relevant information that helps distinguish among the events. In some embodiments, a system or method can hypothesize that phase information between channels is relevant for distinguishing among cardiac events since valves are located at different positions within the heart. Perhaps, one of the most distinctive features of the cardiac events is their relative order of occurrence, which repeats periodically with each heartbeat. Time information extracted from the set of sources can be utilized to localize the occurrence of each source signal within the heart cycle. Therefore, the features proposed here are conceived to provide three aspects: 1) Spectral information, 2) Relations among channels, and 3) Relations among events in the form of relative times of occurrence.

The exemplary embodiments of the system and method proposed here provide a source marking algorithm that allows from the explanation earlier for the marking of the Mitral valve closing (MC), Mitral valve opening (MO), Aortic valve opening (AO), Aortic valve closing (AC), Tricuspid valve closing (TC), Tricuspid valve opening (TO), Pulmonary valve closing (PC) and Pulmonary valve opening (PO) signals. The extracted individual valve vibration objects are aligned into a signal for each of the four valves across multiple heart beats. The chart 700 in FIG. 7A shows the source separation of heart valve opening and closing signals. Line 701 indicates the length or duration of the vibration signal for the Mitral valve closing (M1). Line 702 indicates the length or duration of the vibration signal for the Tricuspid valve closing (T1). Line 703 indicates the length or duration of the vibration signal for the Aortic valve closing (A2). Line 704 indicates length or duration of the vibration signal for the Pulmonic valve closing (P2). Signal 705 indicates the composite vibration signal captured by a particular transducer. Signal 706 indicates the EKG signal captured by the system. Referring to chart 710 of FIG. 7B, the Line 707 indicates the length or duration of the vibration of the Aortic valve opening (AO). Line 708 indicates the length or duration of the vibration of the Pulmonic valve opening (PO). Further note that the lines or signals 709 in FIG. 7A or 711 in FIG. 7B are actually several separated superimposed signals representing the vibration signals from separate sources coming from the mitral valve, tricuspid valve, aortic valve, and pulmonary valve (using less than 4 vibration sensors to extract such separated signals in some embodiments).

In the exemplary embodiments, various novel ways of source separating individual heart vibration events from the composite vibration objects captured via multiple transducers can work on a single package that is embodied by an easy-to-use and portable device. Of course, more complicated embodiments using the techniques described herein can use visual sensors, endoscopy cameras, ultrasound sensors, MRI, CT, PET, EEG and other scanning methods alone or in combination such that the monitoring techniques enable improvement in terms of source separation or identification, and/or marking of events such as heart valve openings, brain spikes, contractions, or even peristaltic movements or vibrations. Although the focus of the embodiments herein are for non-invasive applications, the techniques are not limited to such non-invasive monitoring. The techniques ultimately enable diagnosticians to better identify or associate or correlate detected vibrations or signaling with specific biological events (such as heart valve openings and closings, brain spikes, fetal signals, or pre-natal contractions.)

The exemplary embodiments develop novel methods of source identification, which in one embodiment uses the Pulmonary and Aortic auscultation locations, and in addition possibly the Tricuspid and Mitral auscultation locations, enabling the system to identify individual valve events from the vibrations.

In yet other exemplary embodiments, novel methods of source marking can use the Pulmonary and Aortic auscultation locations, and in addition possibly the Tricuspid and Mitral auscultation locations, enabling the time marking of the occurrence of the individual valve events with respect to the electrocardiogram. Such a system capable and suitable of measuring cardiac time intervals in a simple and non-invasive fashion.

Other exemplary embodiments provide tracking of individual valve signals over time. Such novel methods allow for both short-term and long-term discrimination between signals. Short-term pertains to tracking individual stream when they are captured simultaneously as part of the composite signal. Long-term tracking pertains to tracking individual streams across multiple heart beats, tracking valve signals as they transition in and out during each cardiac cycle.

Some of the exemplary embodiments of a system and method described herein includes an embedded hardware system, the main elements to capture body sounds that can include a sensor unit that captures the body sounds, performs digitization, and further digital processing of the body sounds for noise reduction, filtering and amplification.

It will be apparent to those skilled in the art that various modifications may be made in the present embodiments disclosed without departing from the spirit or scope of the claims. Thus, it is intended that the scope of the embodiments cover the modifications and variations within the scope of the claims recited and provided they come within the scope of the methods and systems described and their equivalents.

What is claimed is:

1. A system for measuring cardiac time intervals, comprising:
   a non-invasive sensor unit comprising a transducer array for capturing electrical signals and composite vibration objects;
   a processor configured to use the captured electrical signals and composite vibration objects to provide the operations of:
      separating a plurality of individual heart vibrations of events of a cardiohemic system from the composite vibration objects by performing source estimation to separate the plurality of individual heart vibration events from the composite vibration objects as separated vibration sources;
      identifying the plurality of individual heart vibration events from the composite vibration objects wherein identification of the separated vibration sources in individual heart beats of the cardiohemic events are associated with heart wall motion, blood motion, and heart valve events;
      marking individual heart events from the plurality of individual heart vibration events with respect to an electrocardiogram signal; and
      presenting the individual heart vibration events on a visual display extracted from body sounds from the composite vibration objects to aid in diagnosing one or more among pulmonary disease, respiratory disease, coronary artery disease, heart murmurs, valve abnormalities, heart failure, heart rhythm abnormalities or arrhythmias, vascular disease, congenital heart disease, cardiac resynchronization and risk factor modification.

2. The system for measuring cardiac time intervals of claim 1, wherein heart valve events comprises one or more among a mitral valve closing and opening, a tricuspid valve closing and opening, an aortic valve opening and closing or a pulmonary valve opening and closing.

3. The system for measuring cardiac time intervals of claim 1, wherein the identification of the separated vibration sources in the individual heartbeats comprises individual vibration signals from a mitral valve, an aortic valve, a tricuspid valve, a coronary artery, murmurs, third sound, fourth sound, a pulmonary valve, a respiratory sound, a breathing sound, a heart wall motion, and a snoring sound.

4. The system for measuring cardiac time intervals of claim 1, wherein the non-invasive sensor unit includes the transducer array having at least one or more pads where at least one of the at least one or more pads comprises at least a vibration sensor and optionally an electrode for an electrocardiogram sensor.

5. The system for measuring cardiac time intervals of claim 1, further comprising a sensor for performing an electrocardiogram and wherein the non-invasive sensor unit comprises at least one among an accelerometer, an acoustic sensor, or a piezoelectric sensor for sensing heart vibrations and wherein the system presents the individual heart valve events with respect to a QRS of the electrocardiogram enabling diagnosticians to correlate detected vibrations or signaling with specific biological events selected among heart valve openings and closings, apnea signals, brain spikes, fetal signals, or pre-natal contractions using the non-invasive sensor unit.

6. The system for measuring cardiac time intervals of claim 1, wherein the processor is further configured to:
   separate sources from the composite signals by source estimation using at least one among machine learning, auditory scene analysis, or sparse coding;
   phase estimate a phase between the separated vibration sources; and
   calculate time stamps for each of the separated vibration sources at each heart beat with respect to a synchronized electrocardiogram signal and one or more sensors of the non-invasive sensor unit.

7. The system of measuring cardiac time intervals of claim 6, wherein a number of vibration sensors in the non-invasive sensor unit is less than the number of the separated vibration sources and wherein the separating of the plurality of individual heart vibrations of events of the cardiohemic system uses one among a visual sensor, an endoscopy camera, an ultrasound sensor, a magnetic resonance imaging device, a computed tomography scanner, a positron emission tomography scanner, or an electroencephalogram scanner alone or in combination to enable improvement in terms of source separation or identification, or marking of events among heart valve openings, brain spikes, contractions, peristaltic movements or peristaltic vibrations.

8. The system for measuring cardiac time intervals of claim 1, wherein the processor is configured to separate the plurality of individual heart vibration events from the composite vibration objects from multichannel signals by decomposing the multichannel signals into sparse activation patterns and clustering the sparse activation patterns.

9. The system for measuring cardiac time intervals of claim 1, wherein the processor is configured to separate the plurality of individual heart vibration events from the composite vibration objects from multichannel signals by decomposing the multichannel signals into sparse activation patterns that appear sparsely across a time chart using a sparse coding module, clustering the sparse activation patterns, and recomposing a plurality of source streams by applying an activation mask to the sparse activation patterns assigned to a cluster using basis elements where time locations of activation patterns are clustered together and assigned to the same source.

10. The system for measuring cardiac time intervals of claim 8, wherein the processor decomposes the multichannel signals obtained from the transducer array having one or more tri-axial accelerometers into sparse activation patterns using a K-SVD algorithm and wherein the identified valve signals are marked to indicate their start and end of the individual heart vibration event with respect to the start of an electrocardiogram.

11. The system for measuring cardiac time intervals of claim 1, wherein the system comprises a wearable device in the form of a patch, band, necklace, belt, or bandage configured to communicate with a wireless node and further configured to capture an electrocardiogram signal synchronized with one or more accelerometer sensors of the non-invasive sensor unit.

12. The system for measuring cardiac time intervals of claim 8, wherein the processor separates the plurality of individual heart valve events from the composite vibration objects from multichannel signals using at least one source separation technique used for extracting the valve heart signals for application in a non-linear time variant system, among Determined Models, Principal Component Analysis (PCA), Independent Component Analysis ICA, Singular Value Decomposition (SVD), Bin-wise Clustering and Permutation posterior probability Alignment, Undetermined Models, Sparseness condition, Dictionary learning, Convolutive models, or K-SVD Matching Pursuit.

13. The system for measuring cardiac time intervals of claim 1, wherein the marking of individual valve events comprises at least the marking of one or more among a Mitral valve opening (MO), Aortic valve opening (AO), Tricuspid valve opening (TO), or Pulmonary valve opening (PO), and wherein it provides tracking of individual valve signals over time for short-term and long-term discrimination between signals.

* * * * *